US009181282B2

(12) United States Patent
Ide et al.

(10) Patent No.: US 9,181,282 B2
(45) Date of Patent: Nov. 10, 2015

(54) ORGANOSILICA COMPOUNDS

(71) Applicant: UNIVERSITEIT GENT, Ghent (BE)

(72) Inventors: Matthias Ide, Sint-Amandsberg (BE); Pascal Van Der Voort, Wilrijk (BE); Patrick Sandra, Ghent (BE); Frederic Lynen, Ghent (BE)

(73) Assignee: UNIVERSITEIT GENT, Ghent (BE)

( * ) Notice: Subject to any disclaimer, the term of this patent is extended or adjusted under 35 U.S.C. 154(b) by 0 days.

(21) Appl. No.: 14/368,046

(22) PCT Filed: Dec. 21, 2012

(86) PCT No.: PCT/EP2012/076685
§ 371 (c)(1),
(2) Date: Jun. 23, 2014

(87) PCT Pub. No.: WO2013/093022
PCT Pub. Date: Jun. 27, 2013

(65) Prior Publication Data
US 2015/0005525 A1    Jan. 1, 2015

(30) Foreign Application Priority Data
Dec. 23, 2011   (EP) .................................... 11195603

(51) Int. Cl.
*C07F 7/08* (2006.01)
*C07F 7/18* (2006.01)
*B01J 20/283* (2006.01)
*B01J 20/286* (2006.01)

(52) U.S. Cl.
CPC ............. *C07F 7/1808* (2013.01); *B01J 20/283* (2013.01); *B01J 20/286* (2013.01); *C07F 7/184* (2013.01); *B01J 2220/82* (2013.01)

(58) Field of Classification Search
CPC ................................................. C07F 7/1808
USPC ........................................................ 556/406
See application file for complete search history.

(56) References Cited

U.S. PATENT DOCUMENTS

| | | | |
|---|---|---|---|
| 2,374,354 A | 4/1945 | Kaplan | |
| 2,524,218 A | 10/1950 | Bersworth | |
| 2,530,147 A | 11/1950 | Bersworth | |
| 3,244,724 A | 4/1966 | Guttmann | |
| 5,057,296 A | 10/1991 | Beck | |
| 5,098,684 A | 3/1992 | Kresge et al. | |
| 5,160,450 A | 11/1992 | Okahara et al. | |
| 6,358,914 B1 | 3/2002 | Gabriel et al. | |
| 7,563,376 B2 | 7/2009 | Oishi | |
| 7,919,177 B2 | 4/2011 | Jiang et al. | |
| 7,947,799 B2 | 5/2011 | Landskron et al. | |
| 2007/0173401 A1* | 7/2007 | Landskron et al. | 502/232 |

OTHER PUBLICATIONS

Asefa et al., "Recent developments in the synthesis and chemistry of periodic mesoporous organosilicas", *Studies in Surface Science and Catalysis*, vol. 141, 2002, pp. 1-26.
Auner, "Reaktionen von $H_2C = CHSiCl_3$ mit LiBu$^t$'", *Z. anorg. allg. Chem*, vol. 558, 1988, pp. 55-86.
Brondani et al., "Polyfunctional Carbosilanes and Organosilicon Compounds. Synthesis *via* Grignard Reactions", *Tetrahedron Letters*, vol. 43, No. 13, 1993, pp. 2111-2114.
Fritz et al., "Zur Spaltung von Si-C-Bindungen in Si-methylierten Carbo-silanen", *Z. anorg. allg. Chem*, vol. 556, 1988, pp. 23-56.
Gao et al., "Dynamic Surface Tension of Aqueous Surfactant Solutions. 6. Compounds Containing Two Hydrophilic Head Groups and Two or Three Hydrophobic Groups and Their Mixtures with Other Surfactants", *JAOCS*, vol. 71, No. 7, 1994, pp. 771-776.
Ide et al., "Spherical mesoporous silica particles by spray drying: Doubling the retention factor of HPLC columns", *Microporous and Mesoporous Materials*, vol. 142, 2011, pp. 282-291.
Inagaki et al., "An ordered mesoporous organosilica hybrid material with a crystal-like wall structure", *Nature*, vol. 416, 2002, pp. 304-307.
International Preliminary Report on Patentability from International Application No. PCT/EP2012/076685 issued Jun. 24, 2014.
International Search Report from International Application No. PCT/EP2012/076685 mailed Oct. 5, 2013.
Kresge et al., "Ordered mesoporous molecular sieves synthesized by a liquid-crystal template mechanism", *Nature*, vol. 359, 1992, pp. 710-712.
Menger et al., "Gemini Surfactants: Synthesis and Properties", *J. Am. Chem. Soc.*, vol. 113, 1991, pp. 1451-1452.
Menger et al., "Gemini Surfactants: A New Class of Self-Assembling Molecules", *J. Am. Chem. Soc.*, vol. 115, 1993, pp. 10083-10090.
Rosen et al., "Relationship of Structure to Properties of Surfactants. 16. Linear Decyldiphenylether Sulfonates", *JAOCS*, vol. 69, No. 1, 1992, pp. 30-33.
Stöber et al., "Controlled Growth of Monodisperse Silica Spheres in the Micron Size Range", *Journal of colloid and Interface Science*, vol. 26, 1968, pp. 62-69.
Zhao et al., "Triblock Copolymer Syntheses of Mesoporous Silica with Periodic 50 to 300 Angstrom Pores", *Science*, vol. 279, 1998, pp. 548-552.
Zhu et al., "Preparation and Surface Active Properties of Amphipathic Compounds with Two Sulfate Groups and two Lipophilic Alkyl Chains", *JAOCS*, vol. 67, No. 7, 1990, pp. 459-463.
Zhu et al., "Preparation and Properties of Double- or Triple-Chain Surfactants with Two Sulfonate Groups Derived from N-Acyldiethanolamines", *JAOCS*, vol. 68, No. 7, 1991, pp. 539-543.
Zhu et al., "Preparation and Properties of Glycerol-Based Double- or Triple-Chain Surfactants with Two Hydrophilic Ionic Groups", *JAOCS*, vol. 69, No. 7, 1992, pp. 626-632.
Asefa et al., "Periodic mesoporous organosilicas with organic groups inside the channel walls," letters to nature, vol. 402, Dec. 23-30, 1999, pp. 867-871.

* cited by examiner

*Primary Examiner* — Porfirio Nazario Gonzalez
*Assistant Examiner* — Kofi Adzamli
(74) *Attorney, Agent, or Firm* — Merchant & Gould P.C.

(57) ABSTRACT

The present invention relates to novel silica materials, precursors thereof and the preparation thereof. The compounds may be used for a variety of applications, including chromatography and catalysis.

14 Claims, No Drawings

ORGANOSILICA COMPOUNDS

This application is a National Stage Application of PCT/EP2012/076685, filed 21 December 2012, which claims benefit of Ser. No. 11/195,603.3, filed 23 Dec. 2011 in Europe and which applications are incorporated herein by reference. To the extent appropriate, a claim of priority is made to each of the above disclosed applications.

FIELD OF THE INVENTION

The present invention relates to novel silica materials, precursors thereof and the preparation thereof. The compounds may be used for a variety of applications, including separation, microelectronics, sensing optics, electronic printing, controlled drug release and catalysis.

BACKGROUND

Silica is commonly used as stationary phase for chromatography, e.g. High Performance Liquid Chromatography (HPLC). Unlike organic stationary phases, chromatographic silica materials generally provide an improved efficiency and show less evidence of swelling or shrinking. Typically, chromatographic applications employ silica which has been functionalized with an organic group such as octadecyl, octyl, phenyl, amino, cyano and the like.

A disadvantage of silica materials is the presence of residual silanol groups, which may interact with analytes. This may result in excessive peak tailing and irreversible adsorption of some analytes. A further drawback of silica materials is their limited hydrolytic stability. Indeed, the incomplete derivatization of the silica leaves patches of bare silica surface which can be dissolved under alkaline conditions. Furthermore, the silica materials may lose their functional groups under acidic or basic conditions, causing loss of analyte retention and an increase in the concentration of surface silanol groups.

Various solutions to overcome these problems have been developed.

U.S. Pat. No. 7,563,367 (Phenomenex Inc.) describes pH stable chromatographic media using templated multilayer organicinorganic grafting. Although the described compounds exhibit a wider pH range stability as compared to other silica gel sorbents, the functional groups are still easily lost. Furthermore, the preparation of the described compounds requires an extra post synthesis modification step which is not completely reproducible and results in a loss of separation efficiency.

U.S. Pat. No. 7,919,177 (Waters Technologies Corporation) describes porous inorganic/organic hybrid particles having a chromatographically-enhancing pore geometry, which may be surface modified. However, the particles still are unstable at increased pH.

U.S. Pat. No. 7,947,799 (Landskron et al.) describes silica based mesoporous films having an increased number of bridging organic groups. Although these materials have an increased mechanical stability, the short bridging organic groups have a limited influence on separation efficiency.

Accordingly, there is still a need for improved stationary phases for chromatography. More particular, there is a need for silica material to which a functional group is or can be bound which cannot be removed by an acidic or alkaline solution.

SUMMARY OF THE INVENTION

The present invention relates to novel (organo)silica materials and the preparation thereof. The present invention further relates to precursor compounds for use in the preparation of said silica materials. The silica materials according to the present invention may be used for a variety of applications, including chromatography and catalysis.

In a first aspect, the present invention provides a compound of formula (A):

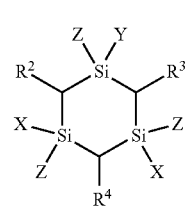

(A)

wherein X is $OR^1$, wherein $R^1$ is $C_{1-6}$alkyl;
Y is X or $-CHR^{13}Si(X)_{3-n}(Z)_n$, wherein n is 1 or 2;
Z is X or $C_{1-4}$alkyl; and
$R^2$, $R^3$, $R^4$ and $R^{13}$ are hydrogen or a hydrocarbon selected from the group consisting of $C_{3-30}$alkyl, $C_{6-10}$aryl, $C_{1-10}$alkyl$C_{6-10}$arylene, $C_{6-10}$aryl$C_{1-6}$alkylene, $C_{3-8}$cycloalkyl, $C_{2-30}$alkenyl, $C_{2-30}$alkynyl, and $C_{2-10}$alkenyl$C_{6-10}$arylene, said hydrocarbon being optionally substituted by one or more substituents;
with the proviso that $R^2$, $R^3$, $R^4$ and $R^{13}$ are not all hydrogen.

In particular embodiments, said one or more substituents are independently selected from hydroxyl, epoxy, $C_{1-30}$thioalkyl, halo, amino, sulfhydryl, acyl, $C_{1-10}$alkoxy, $C_{1-6}$alkyl, $C_{1-6}$alkylamino, sulfophenyl, carboxyl, cyano, methylcyano, phenyl, 2,3-dihydroxypropyl, styryl, divinylphenyl, ethylvinylphenyl, pentafluorophenyl, sulfo, sulfonato, phosphonato, phosphinato, $-SOCl$, $-NH_3R^{12}$ wherein $R^{12}$ is a counterion, phenyloxy$C_{1-6}$alkyl, allylamino, allyl, benzoyloxy, tolyl, nitrophenyl, oxyphenyl, an ion exchange functionality, an embedded polar functionality and ethylpyridinyl.

In a further aspect, the present invention provides a composition comprising a compound of formula (B) and a compound of formula (C):

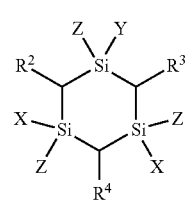

(B)

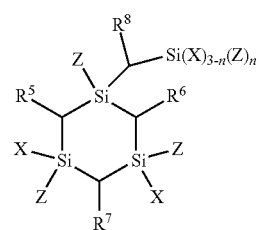

(C)

wherein X is $OR^1$, wherein $R^1$ is $C_{1-6}$alkyl;
n is 1 or 2;
Z is X or $C_{1-4}$alkyl; and
$R^2$, $R^3$, $R^4$, $R^5$, $R^6$, $R^7$ and $R^8$ are hydrogen or a hydrocarbon selected from the group consisting of $C_{3-30}$alkyl, $C_{6-10}$aryl, $C_{1-10}$alkyl$C_{6-10}$arylene, $C_{6-10}$aryl$C_{1-6}$alkylene, $C_{3-8}$cycloalkyl, $C_{2-30}$alkenyl, $C_{2-30}$alkynyl, and $C_{2-10}$alkenyl$C_{6-10}$arylene, said hydrocarbon being optionally substituted by one or more substituents;
with the proviso that $R^2$, $R^3$ and $R^4$ are not all hydrogen and $R^5$, $R^6$ $R^7$ and $R^8$ are not all hydrogen.

In particular embodiments, the composition comprises compounds of formula (D), (E), (F), (G) and (H):

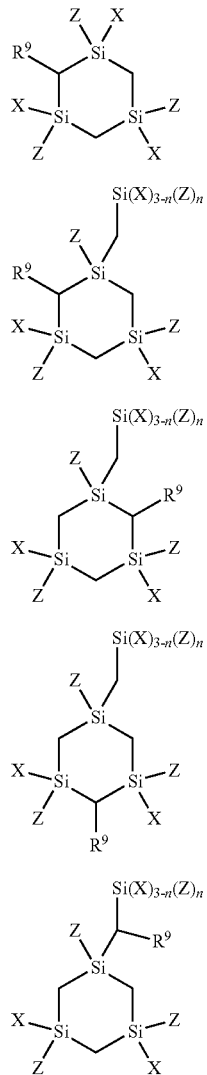

wherein X is $OR^1$, wherein $R^1$ is $C_{1-6}$alkyl;
n is 1 or 2;
Z is X or $C_{1-4}$alkyl; and
$R^9$ is a hydrocarbon selected from the group consisting of $C_{3-30}$alkyl, $C_{6-10}$aryl, $C_{1-10}$alkyl$C_{6-10}$arylene, $C_{6-10}$aryl$C_{1-6}$alkylene, $C_{3-8}$cycloalkyl, $C_{2-30}$alkenyl, $C_{2-30}$alkynyl, and $C_{2-10}$alkenyl$C_{6-10}$arylene, said hydrocarbon being optionally substituted by one or more substituents.

In a further aspect, the present invention provides the use of the compound (A) or a composition as described above, for preparing a porous material.

In a further aspect, the present invention provides a (silica) material comprising $[SiC]_3$ ring compounds of formula (A), (B), (C), (D), (E), (F), (G) and/or (H), wherein said $[SiC]_3$ rings are interconnected by oxygen atoms O via Si—O bonds.

In particular embodiments, said material is a porous material. In certain embodiments, said material is formed as a powder, a film or a monolith.

In particular embodiments, said material further comprises $[SiC]_3$ ring compounds of formula (I):

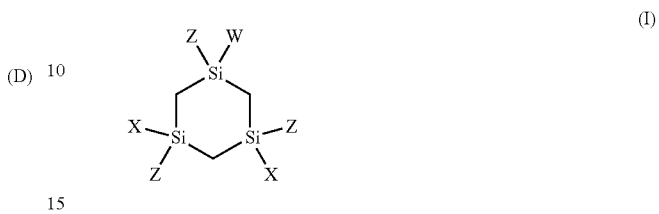

wherein X is $OR^1$, wherein $R^1$ is $C_{1-6}$alkyl;
W is X or $CH_2Si(X)_{3-n}(Z)_n$, wherein n is 1 or 2;
Z is X or $C_{1-4}$alkyl;
wherein the $[SiC]_3$ rings of formula (A) and (I) are interconnected by oxygen atoms O via Si—O bonds.

In certain embodiments, the material according to the present invention further comprises acyclic units $SiO_4$ or $SiO_3R^{10}$, wherein $R^{10}$ is $C_{1-6}$alkyl and wherein the $[SiC]_3$ rings and the acyclic units are interconnected by the O atoms.

In a further aspect, the present invention provides a stationary phase for chromatography, comprising the material as described above.

In a further aspect, the present invention provides the use of the material as described above as a stationary phase for chromatography.

In a further aspect, the present invention provides a method for the preparation of a compound of formula (A) as described herein, said method comprising the reaction of a compound of formula (I) as described above with a compound Q-R, wherein Q is halo and R is a hydrocarbon selected from the group consisting of $C_{3-30}$alkyl, $C_{6-10}$aryl, $C_{1-10}$alkyl$C_{6-10}$arylene, $C_{6-10}$aryl$C_{1-6}$alkylene, $C_{3-8}$cycloalkyl, $C_{2-30}$alkenyl, $C_{2-30}$alkynyl, and $C_{2-10}$alkenyl$C_{6-10}$arylene, said hydrocarbon being optionally substituted by one or more substituents, in the presence of a strong base selected from IUPAC Group 1 metal alkyl compounds, IUPAC Group 1 metal aryl compounds, lithium diisopropylamide, lithium diethylamide, lithium dimethylamide, lithium dicyclohexylamide, sodium amide, lithium bis(trimethylsilyl)amide, sodium hydride, lithium hexamethyldisilazide and sodium hexamethyldisilazide.

In a further aspect, the present invention provides a method for the preparation of a material comprising $[SiC]_3$ ring compounds as described above, comprising the step of polycondensing a compound of formula (A), (B), (C), (D), (E), (F), (G) and/or (H) under conditions suitable for polycondensation of said compound, optionally in the presence of a template material selected from the group consisting of non-ionic surfactants, ionic surfactants, colloidal crystals, polymers, hyper branched molecules, star-shaped molecules, macromolecules, dendrimers, and combinations thereof under conditions suitable for self-assembly of said compound and removing the template material from the self-assembled cyclic molecule.

In particular embodiments, said template material is selected from a poloxamer, a tetraalkylammonium salt, a nonionic polyoxyethylene alkyl and a Gemini surfactant.

In certain embodiments, the method for the preparation of a material comprising $[SiC]_3$ ring compounds according to the present invention further comprises the step of spray-drying a composition comprising the compound of formula of formula (A), (B), (C), (D), (E), (F), (G) and/or (H), optionally in the presence of said template material.

The silica materials according to the present invention have various advantages over the silica materials for chromatography which are commercially available. First, the functional groups are attached to the silica material via C—C bonds, which are stronger and more stable compared to C—O—Si bonds. This prevents the loss of functional groups, even at low or high pH, and therefore ensures stable analyte retention. Furthermore, the functionalization of [Si—C]$_3$ rings followed by polycondensation of these rings ensures a high and uniform presence of functional groups in the silica material. The materials according to the present invention further comprise [Si—C]$_3$ rings which are interconnected to other rings with three Si—O bonds, which ensure a high mechanical and hydrolytic stability of the silica material. The silica materials according to the present invention may further be produced as uniform spheres without mesoporosity, or with a controlled and ordered (meso)porosity.

Due to the increased stability of the silica materials according to the present invention, these materials may be used as stationary phase for chromatographic analysis at the complete pH range (1-14). The present silica materials can further result in significantly increased retention factors, and may therefore allow better separations. Moreover, the use of the present silica materials as a stationary phase may allow separation on a water gradient, which is more economical and environmentally friendly compared to solvent gradients.

DETAILED DESCRIPTION

The present invention will be described with respect to particular embodiments but the invention is not limited thereto. Any reference signs in the claims shall not be construed as limiting the scope thereof.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The terms "comprising", "comprises" and "comprised of" also include the term "consisting of".

Furthermore, the terms first, second, third and the like in the description and in the claims, are used for distinguishing between similar elements and not necessarily for describing a sequential or chronological order, unless specified. It is to be understood that the terms so used are interchangeable under appropriate circumstances and that the embodiments of the invention described herein are capable of operation in other sequences than described or illustrated herein.

The term "about" as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

The recitation of numerical ranges by endpoints includes all numbers and fractions subsumed within the respective ranges, as well as the recited endpoints.

All documents cited in the present specification are hereby incorporated by reference in their entirety.

Unless otherwise defined, all terms used in disclosing the invention, including technical and scientific terms, have the meaning as commonly understood by one of ordinary skill in the art to which this invention belongs. By means of further guidance, definitions for the terms used in the description are included to better appreciate the teaching of the present invention. The terms or definitions used herein are provided solely to aid in the understanding of the invention.

Unless expressly stated otherwise, each of the following terms has the indicated meaning:

The term "Acyl" or "carbonyl" refers to a radical formed by removal of the hydroxy from a carboxylic acid (i.e., R—C(=O)—). Preferred acyl groups include acetyl, formyl, and propionyl, with acetyl being most preferred.

The term "$C_{1-6}$alkyl", as a group or part of a group, refers to a hydrocarbyl radical of Formula $C_nH_{2n+1}$ wherein n is a number ranging from 1 to 6. Generally, the alkyl groups comprise from 1 to 6 carbon atoms, for example 1 to 4 carbon atoms. Alkyl groups may be linear, or branched and may be substituted as indicated herein. When a subscript is used herein following a carbon atom, the subscript refers to the number of carbon atoms that the named group may contain. Thus, for example, $C_{1-4}$alkyl means an alkyl of 1, 2, 3 or 4 carbon atoms. Examples of alkyl groups are methyl, ethyl, propyl, isopropyl, butyl, isobutyl, sec-butyl, tert-butyl, pentyl and its chain isomers, hexyl and its chain isomers.

The term "$C_{2-6}$alkenyl" by itself or as part of another substituent, refers to an unsaturated hydrocarbyl group, which may be linear, or branched, comprising one or more carbon-carbon double bonds. Preferred alkenyl groups thus comprise between 2 and 6 carbon atoms, preferably between 2 and 4 carbon atoms. Non-limiting examples of $C_{2-6}$alkenyl groups include ethenyl, 2-propenyl, 2-butenyl, 3-butenyl, 2-pentenyl and its chain isomers, 2-hexenyl and its chain isomers, 2,4-pentadienyl and the like.

The term "$C_{2-6}$alkynyl" by itself or as part of another substituent, refers to an unsaturated hydrocarbyl group, which may be linear, or branched, comprising one or more carbon-carbon triple bonds. Preferred alkynyl groups thus comprise between 2 and 6 carbon atoms, preferably between 2 and 4 carbon atoms. Non limiting examples of $C_{2-6}$alkynyl groups include ethynyl, 2-propynyl, 2-butynyl, 3-butynyl, 2-pentynyl and its chain isomers, 2-hexynyl and its chain isomers and the like As used herein, the term "$C_{3-8}$cycloalkyl", by itself or as part of another substituent, refers to a saturated or partially saturated cyclic alkyl radical containing from about 3 to about 8 carbon atoms. Examples of $C_{3-8}$cycloalkyl include cyclopropyl, cyclobutyl, cyclopentyl, or cyclohexyl, cycloheptyl and cyclooctyl.

As used herein, the term "$C_{6-10}$aryl", by itself or as part of another substituent, refers to a polyunsaturated, aromatic hydrocarbyl group having a single ring (i.e. phenyl) or multiple aromatic rings fused together (e.g. naphthalene), or linked covalently, typically containing 6 to 10 atoms; wherein at least one ring is aromatic. Aryl rings may be unsubstituted or substituted with from 1 to 4 substituents on the ring. Aryl may be substituted with halo, cyano, nitro, hydroxy, carboxy, amino, acylamino, alkyl, heteroalkyl, haloalkyl, phenyl, aryloxy, alkoxy, heteroalkyloxy, carbamyl, haloalkyl, methylenedioxy, heteroaryloxy, or any combination thereof. Examples of $C_{6-10}$aryl include phenyl, naphthyl, indanyl, or 1,2,3,4-tetrahydro-naphthyl.

The term "styryl" as used herein refers to the univalent radical $C_6H_5$—CH=CH— derived from styrene.

When the term "alkyl" is used as a suffix following another term, as in "hydroxyalkyl," this is intended to refer to an alkyl group, as defined above, being substituted with one or two (preferably one) substituent(s) selected from the other, specifically-named group, also as defined herein. The term "hydroxyC$_{1-4}$alkyl" therefore refers to a —R$^a$—OH group wherein R$^a$ is C$_{1-4}$alkyl as defined herein. The term "C$_{1-6}$alkoxy" or "C$_{1-6}$alkyloxy" as used herein refers to a radical having the formula —OR$^d$ wherein R$^d$ is C$_{1-6}$alkyl. Non-limiting examples of suitable alkoxy include methoxy, ethoxy, propoxy, isopropoxy, butoxy, isobutoxy, sec-butoxy, tert-butoxy, pentyloxy and hexyloxy. The term "C$_{1-30}$thioalkyl" as used herein refers to a radical having the formula —SR$^z$ wherein R$^z$ is C$_{1-30}$alkyl. Non-limiting examples of suitable thioalkyl include thiomethyl, thioethyl, thiopropyl, thio-isopropyl, thiobutyl, thio-isobutyl, thio-sec-butyl, thio-tert-butyl, thiopentyl, thiohexyl and thiooctadecyl.

As used herein, the term "C$_{1-6}$alkylene", by itself or as part of another substituent, refers to C$_{1-6}$alkyl groups that are divalent, i.e., with two single bonds for attachment to two other groups. Alkylene groups may be linear or branched and may be substituted as indicated herein. Non-limiting examples of alkylene groups include methylene (—CH$_2$—), ethylene (—CH$_2$—CH$_2$—), methylmethylene (—CH(CH$_3$)—), 1-methyl-ethylene (—CH(CH$_3$)—CH$_2$—), n-propylene (—CH$_2$—CH$_2$—CH$_2$—), 2-methylpropylene (—CH$_2$—CH(CH$_3$)—CH$_2$—), 3-methylpropylene (—CH$_2$—CH$_2$—CH(CH$_3$)—), n-butylene (—CH$_2$—CH$_2$—CH$_2$—CH$_2$—), 2-methylbutylene (—CH$_2$—CH(CH$_3$)—CH$_2$—CH$_2$—), 4-methylbutylene (—CH$_2$—CH$_2$—CH$_2$—CH(CH$_3$)—), pentylene and its chain isomers, hexylene and its chain isomers. The term "C$_{6-10}$arylC$_{1-6}$alkylene", as a group or part of a group, means a C$_{1-6}$alkyl as defined herein, wherein a hydrogen atom is replaced by a C$_{6-10}$aryl as defined herein. Examples of C$_{6-10}$arylC$_{1-6}$alkyl radicals include benzyl, phenethyl, dibenzylmethyl, methylphenylmethyl, 3-(2-naphthyl)-butyl, and the like.

As used herein, the term "C$_{1-6}$alkylC$_{6-10}$arylene", by itself or as part of another substituent, refers to a C$_{6-10}$aryl group as defined herein, wherein a hydrogen atom is replaced by a C$_{1-6}$alkyl as defined herein. As used herein, the term "C$_{3-6}$cycloalkylene", by itself or as part of another substituent refers to a saturated homocyclic hydrocarbyl biradical of formula C$_n$H$_{2n-2}$. Non-limiting examples of cycloalkylene include 1,2-cyclopropylene, 1,1-cyclopropylene, 1,1-cyclobutylene, 1,2-cyclobutylene, 1,3-cyclopentylene, 1,1-cyclopentylene, or cyclohexylene.

The term "aminoC$_{1-6}$alkyl", by itself or as part of another substituent, refers to the group —R$^j$—NR$^k$R$^l$ wherein R$^j$ is C$_{1-6}$alkylene, R$^k$ is hydrogen or C$_{1-6}$alkyl as defined herein, and R$^l$ is hydrogen or C$_{1-6}$alkyl as defined herein.

The term "C$_{1-6}$alkyl ether" also referred as "C$_{1-6}$alkoxy C$_{1-6}$alkyl", by itself or as part of another substituent, refers to an C$_{1-6}$alkyl group substituted with one to two R$^b$, wherein R$^b$ is C$_{1-6}$alkoxy as defined below.

The term "C$_{2-6}$alkenyl ether" also referred as "C$_{1-6}$alkenyloxyC$_{1-6}$alkenyl", by itself or as part of another substituent, refers to an C$_{1-6}$alkenyl group substituted with one to two R$^e$, wherein R$^e$ is C$_{1-6}$alkenyloxy.

"Halo" or "halogen" is fluoro, chloro, bromo or iodo.

The term "sulfhydryl", by itself or as part of another substituent, refers to an —SH group.

The term "sulfo", by itself or as part of another substituent, refers to a —SO$_3$H group or a salt thereof.

The term "sulfonato", by itself or as part of another substituent, refers to a —SO$_4$H group or a salt thereof.

The term "phosphanato", by itself or as part of another substituent, refers to the radical —P(O)(OR$^{aa}$)$_2$. The term "phosphinato", by itself or as part of another substituent, refers to the radical —PR$^{aa}$(O)(OR$^{aa}$), where each R$^{aa}$ can be selected from, for example, hydrogen, alkyl, alkenyl, alkynyl, aryl, arylalkyl, cycloalkyl, haloalkyl, heteroaryl, and heterocyclyl.

The term "amidyl", by itself or as part of another substituent, refers to R$^{bb}$C(O)N(R$^{bb}$)—, wherein R$^{bb}$ and R$^{bb}$ are each independently a hydrogen atom, an alkyl group, an aryl group, a cycloalkyl, a heteroalkyl, a heterocycloalkyl or a heteroaryl.

The term "amino" by itself or as part of another substituent, refers to NH$_2$.

The term "azido", by itself or as part of another substituent, refers to —N$_3$.

The term "epoxy", by itself or as part of another substituent, refers to an oxygen atom, which is bound to two adjacent carbon atoms, thereby forming an oxirane moiety.

The term "porous" as used herein refers to solid materials with pores, i.e. cavities, channels or interstices, which are deeper than they are wide. Quantitatively, the "porosity" of a porous solid is defined as the fraction E of the apparent volume of the material (V), which is attributed to the pores (Vp). Thus, the porosity is given by E=Vp/V.

The term "mesoporous" as used herein refers to solid materials having pores within the range of from 2 nm to 50 nm. Pores are considered uniform when the standard deviation on the pore diameter is smaller than 25% of the pore diameter.

The term "periodic porous" as used herein means having an ordered arrangement of pores in terms of translation symmetry. Examples of periodic porous materials include periodic mesoporous organosilicas (PMOs), e.g. as described by Asefa et al. (*Nature* 1999, 402, 867-871 and *Studies in Surface Science and Catalysis* 2002, 141, 1-26, which are hereby incorporated herein by reference).

The term "organosilica" as used herein refers to an organosilane compound that comprises organic groups bound to two or more Si atoms.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In a first aspect, the present invention provides methods for the preparation of a compound (A):

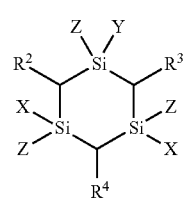

(A)

wherein X is OR$^1$, wherein R$^1$ is C$_{1-6}$alkyl;
Y is X or —CHR$^{13}$Si(X)$_{3-n}$(Z)$_n$, wherein n is 1 or 2;
Z is X or C$_{1-4}$alkyl, for example methyl;

$R^2$, $R^3$, $R^4$ and $R^{13}$ are independently hydrogen or a hydrocarbon selected from the group consisting of $C_{3-30}$alkyl, $C_{6-10}$aryl, $C_{1-10}$alkyl$C_{6-10}$arylene, $C_{6-10}$aryl$C_{1-6}$alkylene, $C_{3-8}$cycloalkyl, $C_{2-30}$alkenyl, $C_{2-30}$alkynyl, and $C_{2-10}$alkenyl$C_{6-10}$arylene, said hydrocarbon being optionally substituted by one or more substituents; with the proviso that $R^2$, $R^3$, $R^4$ and $R^{13}$ are not all hydrogen.

In particular embodiments, $R^2$, $R^3$, $R^4$ and $R^{13}$ are independently hydrogen or a hydrocarbon selected from the group consisting of $C_{4-30}$alkyl, $C_{6-10}$aryl, $C_{1-10}$alkyl$C_{6-10}$arylene, $C_{6-10}$aryl$C_{1-6}$alkylene, $C_{3-8}$cycloalkyl, $C_{4-30}$alkenyl, $C_{4-30}$alkynyl, and $C_{2-10}$alkenyl$C_{6-10}$arylene, said hydrocarbon being optionally substituted by one or more substituents; with the proviso that $R^2$, $R^3$, $R^4$ and $R^{13}$ are not all hydrogen.

In certain embodiments, $R^2$, $R^3$, $R^4$ and $R^{13}$ are independently hydrogen or a hydrocarbon selected from the group consisting of $C_{6-30}$alkyl, $C_{3-20}$alkenyl, and $C_{3-20}$alkynyl, said hydrocarbon being optionally substituted by one or more substituents, with the proviso that $R^2$, $R^3$, $R^4$ and $R^{13}$ are not all hydrogen. In particular embodiments, said $C_{6-30}$alkyl is $C_{8-30}$alkyl, more particularly a $C_{10-30}$alkyl, most particularly $C_{18-30}$alkyl, for example $C_{30}$alkyl. In certain embodiments, said $C_{5-30}$alkyl is $C_{5-20}$alkyl, more particularly $C_{8-20}$alkyl, most particularly $C_{10-20}$alkyl.

In certain embodiments, said $C_{3-20}$alkenyl is $C_{3-18}$alkenyl, more particularly $C_{3-10}$alkenyl, most particularly $C_{3-6}$alkenyl, for example 2-propenyl or 5-hexenyl.

In particular embodiments, $R^2$, $R^3$, $R^4$ and $R^{13}$ are hydrogen or $C_{4-18}$alkyl, $C_{4-18}$alkenyl, or $C_{4-18}$alkynyl; more particularly $C_{8-18}$alkyl, $C_{8-18}$alkyl, or $C_{8-18}$alkyl said alkyl, alkenyl, or alkynyl being optionally substituted by one or more substituents; with the proviso that $R^2$, $R^3$, $R^4$ and $R^{13}$ are not all hydrogen.

In certain embodiments, three of $R^2$, $R^3$, $R^4$ and $R^{13}$ are hydrogen.

In certain embodiments, $R^{13}$ is hydrogen, with the proviso that $R^2$, $R^3$ and $R^4$ are not all hydrogen.

In particular embodiments, Y and Z are hydrogen if X is hydrogen.

In certain embodiments, Z is X. In particular embodiments, Y is X.

In particular embodiments, said one or more substituents are independently selected from hydroxyl, epoxy, benzyl, $C_{1-30}$thioalkyl, halo, amino, sulfhydryl, acyl, $C_{1-10}$alkoxy, amino$C_{1-6}$alkyl, $C_{1-6}$alkylamino (e.g. methylamino and dimethylamino), sulfophenyl, carboxyl, cyano, methylcyano, a nitroterephtalic acid substituent, phenyl, dihydroxypropyl (e.g. 2,3-dihydroxypropyl), styryl, divinylphenyl, polystyrenedivenylphenyl, an acrylate group, a metacrylate group, ethylvinylphenyl, pentafluorophenyl, a complex (e.g. L-proline copper complex, amino acid metal complex, L-hydroxyproline-$Cu^{2+}$ complex) substituent, a 3,5-dinitrobenzoyl substituted L-phenylglycine substituent, a cellulose tris-3,5-dimethylphenylcarbamate substituent, an alpha-acid glycoprotein substituent, an amylose tris-3,5-dimethylphenylcarbamate substituent, sulfo, sulfonato, sulfamoyl, sulfo$C_{1-6}$alkyl (e.g. sulfopropyl), phosphonato, phosphinato, dextranyl, a protein (e.g. lentil lectin, protein A, protein G, wheat germ agglutinin, ovomucoid, concanavalin A, alpha1-acid glycoprotein, bovine serum albumin, human serum albumin), amidyl, a glycopeptide teicoplanin substituent, a crown ether substituent, a cellulose tris(phenyl carbamate) substituent, a (R)-phenylglycine substituent, a 3,5-dinitroaniline urea substituent, —SOCl, —$NH_3R^{12}$, an arsenic acid substituent, a selenic acid substituent, phenyloxy$C_{1-6}$alkyl, a cellulose tris (3-chloro-4-methylphenylcarbamate) substituent, a cellulose tris(4-methylbenzoate) substituent, a cellulose tris(4-chloro-3-methyl-phenylcarbamate) substituent, a cellulose tris(5-chloro-2-methyl-phenylcarbamate) substituent, a cibacron blue substituent, heparinyl, cyclodextrinyl (e.g. alpha-cyclodextrinyl, beta-cyclodextrinyl or gamma-cyclodextrinyl), a (R)-phenylglycine-3,5-dinitrobenzoic acid substituent, a (R)-1-naphtylglycine-3,5-dinitrobenzoic acid substituent, a (S)-valine-3,5-dinitroaniline substituent, a (S)-tert-leucine-3,5-dinitroaniline substituent, a (R)-phenylglycine-3,5-dinitroaniline substituent, a (S)valine-(R)-1-(alpha-naphtyl) ethylamine substituent, a (S)poline-(R)-1(alpha-naphtyl) ethylamine substituent, a (S)-tert-leucine-(S)-1-(alpha-naphtyl)ethylamine substituent, a (S)-tert-leucine-(R)-1-(alpha-naphtyl)ethylamine substituent, a (S)-indoline-2-carboxylic acid-(R)-1-(alpha-naphtyl)ethylamine urea substituent, a (D)-penicillamine substituent, an amylose tris (5-chloro-2-methylphenylcarbamate) substituent, a D-dinitrobenzoyl phenylglycine substituent, a L-dinitrobenzoyl phenylglycine substituent, a (S)-indoline-2-carboxylic acid-(S)-1(alpha-naphtyl)ethylamine urea substituent, a chiral Schiff base substituent, a (L)tartaric acid-mono-(L)-valine-(S)-1-(alpha-naphtyl)ethylamide substituent, acetoxy, N-(acetylglycyl)-3-aminopropyl, 2-acryloxy, 3-(N-allylamino), allylamino, allyl, an aminophenoxy substituent, an aminophenol substituent, azidosulfonyl, benzoyloxy, n-methylbenzamido, a phthalocyanato-metal substituent, succinimidyloxy, tolyl, nitrophenyl, oxyphenyl, an ion exchange functionality, an embedded polar functionality, $C_{1-6}$alkyl (e.g. diisobutyl, isopropyl, . . . ), an amino acid (L or D), ethylpyridinyl, morpholino, cellulosyl, mylosyl and chitosanyl; wherein $R^{12}$ is a suitable counterion, preferably selected from $Br^-$, $Cl^-$, $I^-$ and $NO_3^-$.

In certain embodiments, said one or more substituents are independently selected from hydroxyl, epoxy, $C_{1-30}$thioalkyl, benzyl, halo, amino, sulfhydryl, acyl, $C_{1-10}$alkoxy, $C_{1-6}$alkyl, $C_{1-6}$alkylamino, sulfophenyl, carboxyl, cyano, methylcyano, phenyl, 2,3-dihydroxypropyl, styryl, divinylphenyl, ethylvinylphenyl, pentafluorophenyl, sulfo, sulfonato, phosphonato, phosphinato, —SOCl, —$NH_3R^{12}$, phenyloxy$C_{1-6}$alkyl, allylamino, allyl, benzoyloxy, tolyl, nitrophenyl, oxyphenyl, an ion exchange functionality, an embedded polar functionality and ethylpyridinyl;
wherein $R^{12}$ is a suitable counterion, preferably selected from $Br^-$, $Cl^-$, $I^-$ and $NO_3^-$.

In particular embodiments, said one or more substituents are independently selected from epoxy, $C_{1-30}$thioalkyl, benzyl, cyano, amino, carboxyl, styryl, and phenyl.

It will be understood by those skilled in the art that the moieties substituted on the hydrocarbon can themselves be substituted, if appropriate. For example, the $C_{1-30}$thioalkyl may carry a substituent on its sulfur atom.

The methods according to the present invention for the preparation of a compound (A) comprise the reaction of a compound of formula (I):

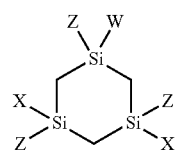

(I)

wherein X is $OR^1$, wherein $R^1$ is $C_{1-6}$alkyl;
W is X or $CH_2Si(X)_{3-n}(Z)_n$, wherein n is 1 or 2;
Z is X or $C_{1-4}$alkyl, for example methyl;

with a compound Q-R in the presence of a strong base, wherein Q is halo and R is a hydrocarbon selected from the group consisting of $C_{3-30}$alkyl, $C_{6-10}$aryl, $C_{1-10}$alkyl$C_{6-10}$arylene, $C_{6-10}$aryl$C_{1-6}$alkylene, $C_{3-8}$cycloalkyl, $C_{2-30}$alkenyl, $C_{2-30}$alkynyl, and $C_{2-10}$alkenyl$C_{6-10}$arylene, said hydrocarbon being optionally substituted by one or more substituents.

Suitable strong bases include IUPAC Group 1 metal alkyl compounds, such as t-butyllithium, n-butyllithium, sec-butyllithium, methyl lithium, n-hexyllithium, 2-ethylhexyl lithium, n-octyllithium, methyl sodium and n-propyl potassium; IUPAC Group 1 metal aryl compounds such as phenyllithium; amides such as lithium diisopropylamide, lithium diethylamide, lithium dimethylamide, lithium dicyclohexylamide, sodium amide and lithium bis(trimethylsilyl)amide; hydrides such as sodium hydride; and azides such as lithium hexamethyldisilazide and sodium hexamethyldisilazide.

In specific embodiments, the strong base is selected from t-butyllithium, n-butyllithium, lithium diisopropylamide, lithium diethylamide, sodium amide, sodium hydride and lithium bis(trimethylsilyl)amide.

In certain embodiments, the strong base is an alkyl lithium such as t-butyllithium, n-butyllithium and methyl lithium. In further embodiments, the strong base is a tertiary alkyl lithium, such as t-butyllithium.

In particular embodiments, the strong base is added to the compound (I) prior to addition of compound Q-R. In particular embodiments, the strong base is added to compound (I) at a temperature between −80° C. and −15° C., for example −78° C. The base is then typically allowed to react with the compound (I) for about 5 to 60 minutes, at a temperature between −80° C. and −15° C. Preferably, the reaction is carried out in a suitable solvent such as tetrahydrofuran (THF), diethyl ether or a mixture thereof. After reaction of the base with compound (I), compound Q-R may be added to the reaction mixture, and the mixture may be allowed to warm up, for example up to room temperature. The mixture is then preferably allowed to react between 1 and 5 hours, for example 3 hours.

The molar ratio of the amount of base to the amount of compound (I) is typically 1 or higher, for example 1.1. The molar ratio of the amount of base to the amount of compound Q-R is typically around 1.

In particular embodiments, the compounds prepared by the preparation method described herein may be further modified in one or more additional reactions. The compounds may be modified further prior to or after polycondensation (see further). For example, the compounds prepared by the preparation method described herein may comprise one or more functional groups which can be modified in a further reaction. As a non-limiting example, the compounds prepared by the preparation method described herein may comprise one or more functional groups which allow for further modification of the compounds via thiol-ene chemistry or click chemistry. Non-limiting examples of such functional groups include thiol, alkene, alkyne, and epoxy moieties.

In a further aspect, the present invention provides a compound of formula (A) as described above. In certain embodiments, the compound of formula (A) is a compound of formula (B), (C), (D), (E), (F), (G) or (H) as described below.

The compound (A) can be obtained via the method comprising the reaction of a compound (I) with a compound Q-R wherein Q is halo and R is a hydrocarbon selected from the group consisting of $C_{3-30}$alkyl, $C_{6-10}$aryl, $C_{1-10}$alkyl$C_{6-10}$arylene, $C_{6-10}$aryl$C_{1-6}$alkylene, $C_{3-8}$cycloalkyl, $C_{2-30}$alkenyl, $C_{2-30}$alkynyl, and $C_{2-10}$alkenyl$C_{6-10}$arylene, said hydrocarbon being optionally substituted by one or more substituents. The compound (I) may be prepared according to the method described by Brondani et al. (*Tetrahedron Lett.* 1993, 34, 2111), which is hereby incorporated by reference. The method described by Brondani et al., herein also referred to as "Brondani method" refers to the synthesis of 1,3,5-tris[diethoxysila]cyclohexane, i.e. compound (I) wherein X and Y are $OR^1$, wherein $R^1$ is ethyl. However, the Brondani method can be generalized for the synthesis of a compound (I). The Brondani method typically results in a mixture comprising compounds (I') and (I''):

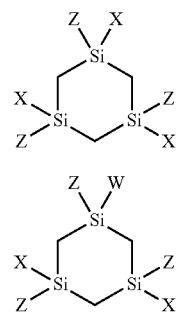

wherein X is $OR^1$, halo, or hydrogen, wherein $R^1$ is $C_{1-6}$alkyl; W is —$CH_2Si(X)_{3-n}(Z)_n$, wherein n is 1 or 2; and Z is X or $C_{1-4}$alkyl, for example methyl.

Compounds (I') and (I'') may or may not be separated prior to reaction with the strong base and compound Q-R as described above. If compounds (I') and (I'') are not separated, the reaction with the strong base and compound Q-R results in a composition comprising compounds (B) and (C):

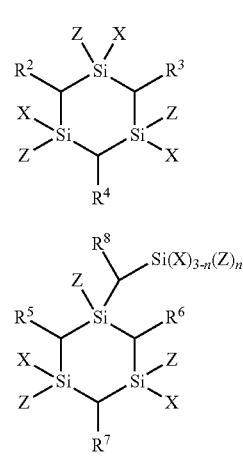

wherein X is $OR^1$, wherein $R^1$ is $C_{1-6}$alkyl;
Z is X or $C_{1-4}$alkyl, for example methyl;
n is 1 or 2;
$R^2$, $R^3$ and $R^4$ are independently hydrogen or a hydrocarbon selected from the group consisting of $C_{3-30}$alkyl, $C_{6-10}$aryl, $C_{1-10}$alkyl$C_{6-10}$arylene, $C_{6-10}$aryl$C_{1-6}$alkylene, $C_{3-8}$cycloalkyl, $C_{2-30}$alkenyl, $C_{2-30}$alkynyl, and $C_{2-10}$alkenyl $C_{8-18}$arylene, said hydrocarbon being optionally substituted by one or more substituents;
$R^5$, $R^6$, $R^7$ and $R^8$ are independently hydrogen or a hydrocarbon selected from a group consisting of $C_{3-38}$alkyl, $C_{8-18}$aryl, $C_{1-10}$alkyl$C_{8-18}$arylene, $C_{8-18}$aryl$C_{1-8}$alkylene, $C_{3-8}$cycloalkyl, $C_{2-38}$alkenyl, $C_{2-38}$alkynyl, and $C_{2-18}$alkenyl $C_{8-18}$arylene, said hydrocarbon being optionally substituted by one or more substituents;

wherein $R^2$, $R^3$ and $R^4$ are not all hydrogen and $R^5$, $R^6 R^7$ and $R^8$ are not all hydrogen.

Accordingly, in a further aspect, the present invention provides a composition comprising a compound (B) and a compound (C) as described above.

In particular embodiments, two of $R^2$, $R^3$ and $R^4$ are hydrogen, and three of $R^5$, $R^6$, $R^7$ and $R^8$ are hydrogen. In compound (C), the relative position of the non-hydrogen substituent $R^5$, $R^6$ or $R^7$ and the —$CR^8Si(X)_{3-n}(Z)_n$ moiety may vary. Accordingly, in particular embodiments, the composition comprising compounds (B) and (C) is a composition comprising compounds (D), (E), (F), (G) and (H):

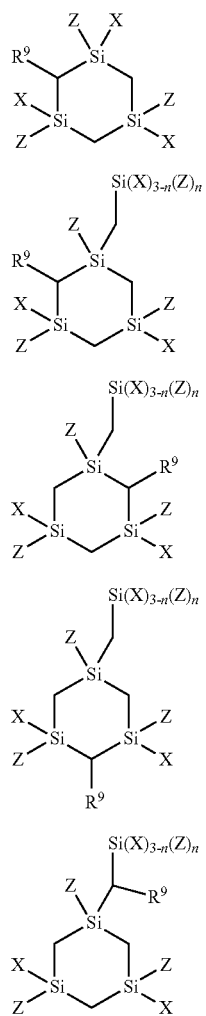

wherein X is $OR^1$, wherein $R^1$ is $C_{1-6}$alkyl;
Z is X or $C_{1-4}$alkyl, for example methyl;
n is 1 or 2 and
$R^9$ is a hydrocarbon selected from the group consisting of $C_{3-30}$alkyl, $C_{6-10}$aryl, $C_{1-10}$alkyl$C_{6-10}$arylene, $C_{6-10}$aryl$C_{1-6}$alkylene, $C_{3-8}$cycloalkyl, $C_{2-30}$alkenyl, $C_{2-30}$alkynyl, and $C_{2-10}$alkenyl$C_{6-10}$arylene, said hydrocarbon being optionally substituted by one or more substituents.

The compounds of formula (A) are useful in the preparation of organosilica materials, which are particularly useful as stationary phases for chromatography.

Accordingly, in a further aspect, the present invention provides a material comprising [SiC]$_3$ ring compounds of formula (A) as described above, wherein said [SiC]$_3$ rings are interconnected by oxygen atoms O via Si—O bonds.

In particular embodiments, the material according to the present invention is a porous material. Porous materials have a significantly larger surface-to-volume ratio as compared to non-porous materials. This is particularly advantageous for use of the material according to the present invention in applications such as chromatography, catalysis, sorption, gas sensing, ion exchange, optics and photovoltaics. In further embodiments, the pores have a diameter in a range from 0.5 nm to 1000 nm. In yet further embodiments, the material according to the present invention is a mesoporous material. In certain embodiments, the pores are uniform.

In particular embodiments, the material according to the present invention is a non-periodic porous material. In other embodiments, the material according to the present invention is a periodic porous material. The periodic porous material may have various pore arrangements, for example a hexagonal arrangement.

In certain embodiments, the material according to the present invention is an ordered mesoporous (organo)silica material. Examples of these materials include but are not limited to M41S materials (Kresge, Nature 1992, 359, 710 & U.S. Pat. No. 5,057,296 1991 & U.S. Pat. No. 5,098,684 1992), SBA materials (Zhao D. Y. Science 1998, 279, 548), PMO materials (Inagaki, S. Nature 2002, 416, 304), KIT-materials and HMS-materials.

In particular embodiments, the material according to the present invention further comprises [SiC]$_3$ ring compounds of formula (I) as described above, wherein the [SiC]$_3$ rings of formula (A) and (I) are interconnected by oxygen atoms O via Si—O bonds.

In certain embodiments, the material according to the present invention further comprises acyclic units $SiO_4$ or $SiO_3R^{10}$, wherein $R^{10}$ is $C_{1-6}$alkyl and wherein the [SiC]$_3$ rings and the acyclic units are interconnected by the O atoms.

The material according to the present invention may be formed as a powder, a film or a monolith. In particular embodiments, the material is formed as a film provided on particles of another material, thereby obtaining core-shell particles. For many applications, such core-shell particles may have similar properties as powders comprising a single material. However, core-shell particles may be less expensive to manufacture and more monodisperse. In certain embodiments, the material is formed as a film coating the interior of a capillary.

The material according to the present invention is particularly useful as a stationary phase for chromatography. Accordingly, in a further aspect, the present invention provides a stationary phase for chromatography, comprising the material as described above. However, the material may also be used in a broader range of applications, for example in microelectronics (e.g. as low-k materials), electronic printing, waste water cleaning, catalysis, sensing optics, controlled drug release and chemical storage.

In a further aspect, the present invention provides a method for the preparation of a material comprising [SiC]$_3$ ring compounds of formula (A) wherein said [SiC]$_3$ rings are interconnected by oxygen atoms O via Si—O bonds, as described above. The method according to the present invention comprises the step of polycondensing a compound (A), or a composition comprising compounds (B) and (C), or a composition comprising compounds (D), (E), (F), (G) and (H) under conditions suitable for polycondensation of said compound(s).

In particular embodiments, the method according to the present invention comprises the step of polycondensing a composition comprising compounds (A) and (I), or a composition comprising compounds (B), (C) and (I), or a composition comprising compounds (D), (E), (F), (G), (H) and (I) under conditions suitable for polycondensation of said compound(s).

In particular embodiments, the method according to the present invention comprises the step of polycondensing a composition comprising compounds (A) and a compound $Si(OR^{11})_4$, or a composition comprising compounds (B), (C) and $Si(OR^{11})_4$, or a composition comprising compounds (D), (E), (F), (G), (H) and a compound $Si(OR^{11})_4$ under conditions suitable for polycondensation of said compound(s), wherein $R^{11}$ is $C_{1-6}$alkyl. In particular embodiments, $R^{11}$ is ethyl.

The fact that the compounds (A) and related compounds are already functionalized with groups such as $R_{2-4}$ prior to polycondensation ensures a high and uniform presence of functional groups in the resulting silica material. Furthermore, the functional groups are attached to the silica material via C—C bonds, which prevents the loss of functional groups, even at low or high pH.

In particular embodiments, the step of polycondensing as described above is carried out in the presence of a template material. The presence of a template material may allow the formation of a mesoporous material. In particular embodiments, the template material is selected from the group consisting of non-ionic surfactants, ionic surfactants, colloidal crystals, polymers, hyper branched molecules, star-shaped molecules, macromolecules, dendrimers, and combinations thereof under conditions suitable for self-assembly of said compound and removing the template material from the self-assembled cyclic molecule.

In certain embodiments, the template material is selected from non-ionic surfactants and ionic surfactants. In particular embodiments, the template material is a poloxamer, a tetraalkylammonium salt, a nonionic polyoxyethylene alkyl, a Gemini surfactant or mixtures thereof. In particular embodiments, the template material is a poloxamer or a tetraalkylammonium salt. Preferred tetraalkylammonium salts are cetyltrimethylammonium halides such as cetyltrimethylammonium chloride or cetyltrimethylammonium bromide (CTAB).

Poloxamers are block copolymers of ethylene oxide and propylene oxide, more particularly nonionic triblock copolymers composed of a central hydrophobic chain of polyoxypropylene (poly(propylene oxide)) flanked by two hydrophilic chains of polyoxyethylene (poly(ethylene oxide)). Specifically, the term "poloxamer" refers to a polymer having the formula $HO(C_2H_4))_a(C_3H_6O)_b(C_2H_4O)_aH$ in which "a" and "b" denote the number of polyoxyethylene and polyoxypropylene units, respectively. Poloxamers are also known by the trade name Pluronic®, for example Pluronic® 123 and Pluronic® F127.

Nonionic polyoxyethylene alkyl ethers are known by the trade name Brij®, for example Brij® 76.

Gemini surfactants are compounds having at least two hydrophobic groups and at least one or optionally two hydrophilic groups per molecule have been introduced. These have become known as "gemini surfactants" in the literature, e.g., Chemtech, March 1993, pp 30-33, and J. American Chemical Soc, 115, 10083-10090 (1993) and the references cited therein. A number of the gemini surfactants are reported in the literature, see for example, Okahara et al., J. Japan Oil Chem. Soc. 746 (Yukagaku) (1989); Zhu et al., 67 JAOCS 7, 459 (July 1990); Zhu et al., 68 JAOCS 7, 539 (1991); Menger et al., J. Am. Chemical Soc. 113, 1451 (1991); Masuyama et al., 41 J. Japan Chem. Soc. 4, 301 (1992); Zhu et al., 69 JAOCS 1, 30 (January 1992); Zhu et al., 69 JAOCS 7, 626 July 1992); Menger et al., 115 J. Am. Chem. Soc. 2, 10083 (1993); Rosen, Chemtech 30 (March 1993); and Gao et al., 71 JAOCS 7, 771 (July 1994). A number of gemini surfactants have also been disclosed in the patent literature including U.S. Pat. No. 5,160,450, U.S. Pat. No. 3,244,724, U.S. Pat. Nos. 2,524,218, 2,530,147, 2,374,354, and U.S. Pat. No. 6,358,914.

The molar ratio of the amount of template material to the total amount of silica compounds selected from (A), (B), (C), (D), (E), (F), (G), (H), (I) and $Si(OR^{11})_4$ depends on the type of template material. If the template material is a poloxamer, a tetraalkylammonium salt, a nonionic polyoxyethylene alkyl, Gemini surfactants or a mixture thereof, the molar ratio of the amount of template material to the total amount of silica compounds typically ranges from 0.1 to 0.5, for example 0.1, 0.2, 0.3, 0.4 or 0.5.

In particular embodiments, the polycondensation is carried out in the presence of an alcohol, preferably a hydroxy$C_{1-4}$ alkyl such as ethanol, butanol, isopropanol or mixtures thereof. The alcohol can act as a dispersing agent, which allows silica particles to grow in a freely dispersed way.

In particular embodiments, the polycondensation is performed using a catalyst, for example an acid catalyst such as HCl.

In particular embodiments, the present method comprises the step of spray-drying a composition comprising the compound (A), and optionally a template material as described above, thereby allowing for polycondensation of compound (A). In particular embodiments, the composition may further comprise compounds (B) and (C), compounds (D), (E), (F), (G) and (H), compound (I) and/or $Si(OR^{11})_4$ as described above. Spray-drying allows the formation of spherical silica particles which are suitable for chromatographic applications. The production of silica particles via spray drying has been described by Ide et al. (*Micropor. Mesopor. Mater.* 2011, 142, 282-291), which is hereby incorporated herein by reference.

Alternatively, spherical silica particles may be obtained via the Stöber process. The Stöber process is a process for the generation of monodisperse particles of silica, and was described in 1968 by Stöber and Fink (see e.g. Stöber W and Fink A, *J. colloid Interf. Sci.* 1968, 26, 62-69, which is hereby incorporated herein by reference). Although the Stöber method has been developed for acyclic silicates, the method can also be used for obtaining silicate materials according to the present invention, for example using a composition comprising ammonia, an alcohol and a compound (A). Typically, the compound (A) is added to ammonia and an alcohol in aqueous solution.

The resulting solution is then stirred, thereby obtaining silica particles. The alcohol is typically a hydroxy$C_{1-4}$alkyl, for example ethanol.

Optionally, the template material may be extracted after the polycondensation reaction as described above. If the template material is a surfactant, the template material may for example be extracted by stirring the silica material in a methanol-HCl solution, or by calcination at a temperature between 300° C. and 450° C. in a $N_2$ atmosphere.

Optionally, the silica material according to the present invention may be hydrophobized further by transforming any remaining silanol groups with a trimethylsilyl group.

In particular embodiments, the silica material may be further modified via one or more functional groups, which are present on the silica material. Typically, the one or more functional groups were already present in the compound (A) prior to polycondensation. As a non-limiting example, the one or more functional groups may allow for thiol-ene chemistry or click chemistry. For example, the one or more functional groups provided on the silica material may be selected from the group consisting of thiol, alkene, alkyne, and epoxy moieties.

In a further aspect, the present invention provides the use of a compound (A), or the use of a composition comprising compounds (B) and (C), or the use of a composition comprising compounds (D), (E), (F), (G) and (H) for preparing a porous material. In particular embodiments, said porous material is a stationary phase for chromatography.

In a further aspect, the present invention provides a stationary phase for chromatography, comprising the material comprising [SiC]$_3$ ring compounds as described above.

The compounds of formula (A) may further be used as a grafting material. Indeed, the compounds may be grafted on certain structures such as powders and capillaries. This leads to a more stable anchored (or grafted) group due to a doubling in the anchoring points and due to the more apolar nature of the anchored group. The powders and capillaries onto which the compounds of formula (A) are grafted may be used for chromatography or other applications. In preferred embodiments, the compounds are grafted on the structures via a Si—O—Si bond between the structure and the compound of formula (A). Typically, this is obtained by reaction between the compound of formula (A) and silanol moieties (Si—OH), which are present on the structures. Silanol moieties can be found on structures comprising silicate glass.

The present invention will be illustrated by the following non-limiting examples.

Examples a) Preparation of 1,3,5[Tris(diethoxy)sila]cyclohexane (TDSCH)

TDSCH was prepared according to a method based on the procedure described by Brondani et al. (*Tetrahedron Lett.* 1993, 34, 2111). A solution of 70 mL 0.5 weight % FeCl$_3$ in dry THF was added to 7 g Mg turnings and stirred until a grey colored mixture was visible. This mixture was kept under an inert atmosphere. Then, a solution of 100 mL 14.2 volume % chloromethyltriethoxysilane in dry THF was added to the mixture and stirred for 32 h at 50° C. the mixture was filtered off and the solvent was removed from the filtrate. Pentane was added to the residue and this mixture was also filtered. After the evaporation of pentane, the residue oil was vacuum distilled to give the title compound with a yield of 55%.

b) Functionalization of TDSCH b1—Functionalization of TDSCH with Octadecyl

In a first step 7.2 mmol TDSCH in 20 mL dry THF is stirred under an inert atmosphere at −78° C. Then, 8 mmol tert-butyllithium is added drop wise to this solution, and the solution is stirred for 30 minutes. Then 7.2 mmol 1-octadecylbromide in 30 mL ethoxyethane is added drop wise to the solution, followed by slowly warming the solution to room temperature. After a three hour reaction time 100 ml of ethoxyethane is added and the solution is washed 10 times with 10 ml of a 0.1 M NaHCO$_3$ solution. The organic fraction is recovered and the excess of solvent is evaporated until a yellow residual oil remains. The residual oil comprises the compound (A1):

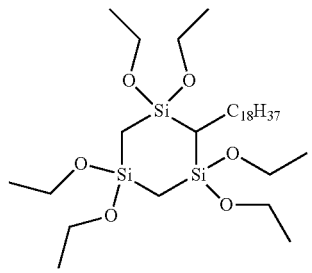

(A1)

wherein C$_{18}$H$_{37}$ represents n-octadecyl.

Similarly, compound (A1) may be prepared by stirring 7.2 mmol TDSCH in 200 mL dry THF under an inert atmosphere at −78° C. Then, 8 mmol tert-butyllithium is added drop wise to this solution, and the solution is stirred for 30 minutes. Then 7.2 mmol 1-octadecylbromide in 2 mL THF is added drop wise to the solution, followed by slowly warming the solution to room temperature. After a three hour reaction time the formed precipitate is filtered off and the solvent is removed from the filtrate by evaporation, leaving a residual oil. The residual oil comprises the compound (A1).

b2—Functionalization of TDSCH with 2-propenyl

In a first step, 1 g of TDSCH was mixed with 20 mL of THF and cooled to −78.5° C. An equimolar amount of tert-butyllithium was added drop wise to this solution and left to stir at −78.5° C. for 30 minutes. A separate solution of 1-bromoprop-2-ene was prepared by dissolving an equimolar amount (relative to TDSCH) of 1-bromoprop-2-ene in 30 mL of ethoxyethane. The solution of 1-bromoprop-2-ene was added drop wise to the solution comprising TDSCH, and the resulting mixture was stirred at room temperature for 24 hours. Hereafter 100 mL of ethoxyethane was added and the solution was washed 10 times with 10 mL of a 0.1 NaHCO$_3$ solution. The organic fraction was recovered and the excess of solvent was evaporated until a clear yellow oil residue remained. The residual oil comprises the compound (A2):

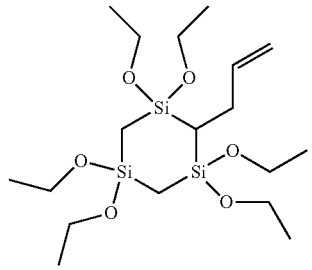

(A2)

Compound (A2) may be modified further as described below (see b5 and b6).

b3—Functionalization of TDSCH with trans-1-bromo-7-methyl-2,6-octadienyl 1 gram of TDSCH was mixed with 20 mL of THF and cooled to −78.5° C. An equimolar amount of tert-butyllithium was added drop wise to this solution, after which the solution was left to stir at −78.5° C. for 30 minutes. A separate solution of trans-1-bromo-7-methyl-2,6-octadiene was prepared by dissolving an equimolar amount (relative to the amount of TDSCH) of trans-1-bromo-7-methyl-2,6-octadiene in 50 mL of ethoxyethane. The solution comprising trans-1-bromo-7-methyl-2,6-octadiene was added drop wise to the mixture comprising TDSCH and the resulting mixture was left to stir at room temperature for 24 h. Subsequently, 100 mL of ethoxyethane was added and the solution was washed 10 times with 10 mL of a 0.1 M NaHCO$_3$ solution. The organic fraction was recovered and the excess of solvent was evaporated until a clear yellow solid residue remained. The residual oil comprises compound (A3):

[SiCH$_2$(OEt)$_2$]$_2$[SiCHCH$_2$CH=CHCH$_2$CH$_2$CH=C(CH$_3$)$_2$(OEt)$_2$].

b4—Functionalization of TDSCH with 3-phenyl-2-propenyl 1 gram of 1,1,3,3,5,5-hexaethoxy-1,3,5-trisilacyclohexane was mixed with 20 mL of THF and cooled to −78.5° C. An equimolar amount of tert-butyllithium was added drop wise to this solution and left to stir at −78.5° C. for 30 minutes. A separate solution of 3-bromo-1-phenyl-1-propene was prepared by dissolving an equimolar amount (relative to TDSCH) of 3-bromo-1-phenyl-1-propene in 30 mL of ethoxyethane. The solution comprising 3-bromo-1-phenyl-1-propene was added drop wise to the mixture comprising TDSCH, and the resulting mixture was left to stir at room temperature for 24 h. Hereafter 100 mL of ethoxyethane was added and the solution was washed 10 times with 10 mL of a 0.1M NaHCO$_3$ solution. The organic fraction was recovered and the excess of solvent was evaporated until a clear yellow liquid residue remained, containing compound (A4): [SiCH$_2$(OEt)$_2$]$_2$[SiCHCH$_2$CH=CHC$_6$H$_5$(OEt)$_2$].

b5—Further Functionalization of Compound (A2) with Thiooctadecyl

Compound (A2) was further functionalized via thiol-ene chemistry. The reaction was performed in a polymerization tube reactor in a substantially oxygen-free atmosphere. The organosilica material was suspended in 10 mL THF, to which 1 w % of Azobisisobutyronitrile (AIBN) and 1.5 molar equivalents of 1-octadecanethiol was added. The reaction was stirred at 70° C. for 6 hours, and leads to compound (A5):

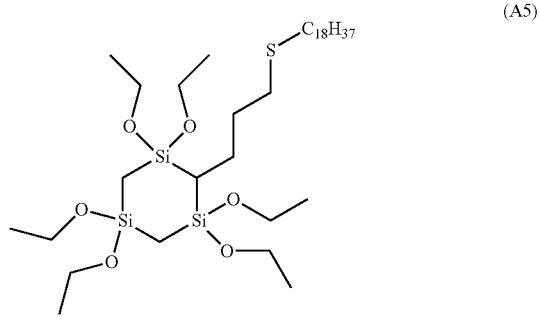

(A5)

wherein C$_{18}$H$_{37}$ represents n-octadecyl.

b6—Further Functionalization of Compound (A2)

The allyl group of compound (A2) was transformed into an oxirane ring as follows. 1 gram of compound (A2) is suspended in 10 mL dichloromethane. To this suspension, a solution of 2.5 gram perbenzoic acid in 10 mL dichloromethane was added. The resulting mixture was stirred at room temperature for 6 hours. Subsequently, the suspension was diluted with 50 mL dichloromethane and washed with a sodium bicarbonate solution. The dichloromethane was then evaporated, until the epoxidized organosilica material remained, i.e. compound (A6):

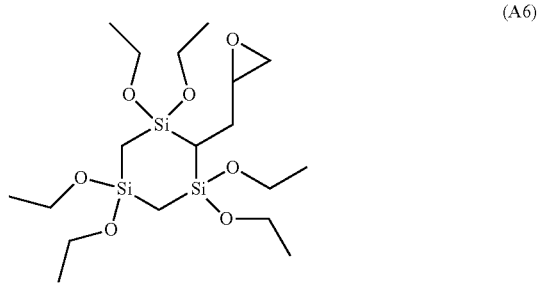 [SMILES: CCO[Si]1(OCC)C[Si](OCC)(OCC)C(CC2CO2)[Si](OCC)(OCC)C1]

(A6)

c) Spray Drying

The organosilica compounds such as compounds (A1) to (A6) as described above may be spray-dried.

The experimental setup typically comprises a mixing step and a spray drying step. In an exemplary mixing step, a solution of H$_2$O, one or more organosilica compounds, HCl and 1-butanol are mixed at room temperature for 15 minutes. For the preparation of ordered mesoporous organosilica powders, the solution may further comprise a template material such as CTAB. Table 1 shows a composition (molar equivalents) of a solution obtained in the mixing step according to a particular embodiment of the present invention. Subsequently this mixture is fed to a spray dryer. This typically results in inorganic-organic hybrid powders, for example M41S type powders, which can be collected by a cyclone separator. The particles are then preferably washed with an acidified ethanol solution (ethanol-HCl) to remove the template material, if present.

Afterwards, the porosity, purity and morphology of the obtained powders can be assessed with x-ray diffraction (XRD), N$_2$-adsorption, elemental analysis and scanning electron microscopy (SEM).

Spray drying can be performed on a Buchi B290 spray dryer with a two-fluid nebulizer connected to pressurized air. A constant heater inlet temperature of 493K and constant outlet temperature of 398K are deemed suitable, and the aspirator may run at a maximum air velocity of 40 m$^3$/h. The nozzle gas flow and the solution feeding speed can be held constant at about 9 L/min and 10% of maximum solution flow respectively.

TABLE 1

| Composition (molar equivalents) of an exemplary spray dry solution | | | | | |
|---|---|---|---|---|---|
| TDSCH | A1 | CTAB | H$_2$O | BuOH | HCl |
| 1 | 0.3 | 0.32 | 3000 | 12 | 7.4 | c1—Preparation of Ordered Mesoporous Spherical Organosilica Particles

Ordered mesoporous organosilica particles were prepared from compound (A2), i.e. [SiCH$_2$(OEt)$_2$]$_2$[SiCHCH$_2$CH=CH(OEt)$_2$], as follows. A solution with the following composition (molar equivalents) is spray dried: [SiCH$_2$(OEt)$_2$]$_2$[SiCHCH$_2$CH=CH(OEt)$_2$]:H$_2$O:HCl:Butanol:CTAB 1:3433:7.6:13.5:0.32. The gas flow was set to 8.93 L/min air and the inlet temperature was 220° C. The final organosilica material was collected with a cyclone separator. The surface area of the organosilica material was 950 m$^2$/g and the pore volume was 0.52 cc/g (cm$^3$/g).

c2—Preparation of Spherical Organosilica Particles

Spherical organosilica particles were prepared from compound (A2) as follows. A solution with the following composition (molar equivalents) is spray dried: [SiCH$_2$(OEt)$_2$]$_2$ [SiCHCH$_2$CH=CH(OEt)$_2$]:H$_2$O:HCl:Butanol:Ethanol 1:3433:7.6:13.5:150. The gas flow was set to 8.93 L/min air and the inlet temperature was 220° C. The final organosilica material was collected with a cyclone separator. The surface area was 8.2 m$^2$/g and the pore volume was 0.01 cc/g.

c3—Preparation of Spherical Organosilica Particles

Spherical organosilica particles were prepared from compound (A3) as follows. A solution with the following composition is spray dried: [SiCH$_2$(OEt)$_2$]$_2$ [SiCHCH$_2$CH=CHCH$_2$CH$_2$CH=C(CH$_3$)$_2$(OEt)$_2$]:H$_2$O: HCl:Butanol:Ethanol 1:3433:7.6:13.5:150. The gas flow was set to 8.93 L/min air and the inlet temperature was 220° C. The final organosilica material was collected with a cyclone separator.

c4—Further Modification of the Organosilica Particles

To remove the double bonds in the particles prepared according to the above paragraph (c3), a hydrogenation reaction was performed on the organosilica particles. 1 gram of organosilica particles was suspended in 20 mL dry toluene with 1 mol % of tris(triphenylphosphine) rhodium chloride, under H$_2$-atmosphere. The mixture was left to stir at room temperature for 10 hours.

d) Evaluation of Organosilica Particles

The chemical stability of the organosilica particles prepared from compound (A2) as described above (see example c2) was compared to the chemical stability of reference organosilica particles. The reference particles were prepared from TDSCH via spray drying, wherein the particles were subsequently functionalized with a C18 (octadecyl) chain through grafting via silanol groups on the particle surface. The TDSCH-based particles are obtained under similar spray drying conditions as used for preparing the organosilica particles obtained from compound (A2).

The chemical stability was assessed via two separate tests. In a first test, the organosilica particles were submitted to a 16-day boiling process in water at 110° C. in an autoclave. In a second test, the particles were submitted to a 2.5 hours stirring process in a 1M sodium hydroxide solution (pH=14). The carbon content of the particles was determined before and after the tests via elemental analysis. As a further reference, also the carbon content of the TDSCH-based particles prior to grafting with a C18 chain was determined. The results are presented in table 2.

TABLE 2

Carbon content of organosilica particles before and after testing

| Particles | Test | C content (m %) |
| --- | --- | --- |
| TDSCH | before test | 11.53 |
| TDSCH-18 | before test | 17.26 |
| TDSCH-18 | boiling | 15.65 |
| TDSCH-18 | NaOH | 12.65 |
| A2 | before test | 18.58 |
| A2 | boiling | 19.03 |
| A2 | NaOH | 18.95 |

The results show that prior to testing, the carbon content of the C18-grafted particles obtained from TDSCH (particles "TDSCH-C18") and of the particles obtained from compound (A2) (particles "A2") is higher than the carbon content of the non-grafted particles obtained from TDSCH (particles "TDSCH"). This confirms that the former particles indeed comprise organic functional groups.

The results further show that after testing, the carbon content of the TDSCH-C18 particles has decreased, indicating that the C18 functional group is removed from the base material when it is boiled in water or when it is treated with 1M of NaOH.

On the other hand, the carbon content of the particles obtained from compound (A2), which have an incorporated functional group prior to the preparation of the particles, is unaffected by the tests. This shows that the organosilica particles described herein, such as the particles obtained from compound (A2), are chemically more stable than organosilica particles functionalized with a C18 chain through grafting.

d) HPLC Evaluation

The suitability of the obtained powders for separation applications can be assessed via HPLC evaluation. To ensure optimal bed stability the column is preferably packed at a 50% higher pressure (900 bar) than the highest operating pressure of the used HPLC system. For example, the particles may be slurry packed at 900 bar with hexane as slurry and packing solvent in a (5 cm×2.1 mm internal diameter, ID) column and evaluated on an Agilent 1200 system with an 80 Hz DAD (Diode Array Detector).

Total Pore Blocking Method

The total pore blocking method can be used to determine the external porosity of the column. The external porosity of a column is a measure for the packing density of that column. The total pore blocking method can be used to determine the external porosity ($\epsilon_e$). The principle works on the repulsion of polar and apolar compounds. First the column is flushed for an hour with isopropanol at 0.2 mL/min to remove all aqueous and organic compounds. After this the column is flushed with decane for 1.5 hours at 0.2 mL/min to make sure all the pores are completely filled with decane. Decane acts as a pore blocking solvent.

The column is then removed from the system and a zero dead-volume connection is fitted. Subsequently the system is flushed with isopropanol at 0.2 mL/min for five minutes. After this the system is flushed with a 10 mM ammonium acetate buffer (pH 3) at 0.2 mL/min for five minutes. Then the column is fitted back in the system and flushed with buffer at 0.1 mL/min for 600 minutes, injecting 0.5 μL of a 1 mg/mL NaI solution. The I$^-$ ion is detected by the detector at 210 nm and acts as a dead time marker.

The external porosity can be calculated as:

$$\epsilon_e = (Ft_0)/V_g \text{ and } V_g = \pi r^2 L$$

wherein $\epsilon_e$, F, $t_0$, $V_g$, r and L are the external porosity, flow rate, retention time of NaI, total column volume, column radius and the column length respectively.

Standard Testing

For the standard column test four test mixtures are made: 1) a mixture of parabenes containing uracil, methyl-4-hydroxybenzoate, ethyl-4-hydroxybenzoate, propyl-4-hydroxybenzoate and butyl-4-hydroxybenzoate (50 μg/mL, each dissolved in 3070 (v/v) acetonitrile/H$_2$O); 2) a phenone mixture comprising uracil, 1-phenyl-1-ethanone, 1-phenyl-1-butanone, 1-phenyl-1-pentanone, 1-phenyl-1-hexanone, 1-phenyl-1-heptanone, 1-phenyl-1-octanone, 1-phenyl-1-decanone and 1-phenyl-1-dodecanone (50 μg/mL, each dissolved in 5050 (v/v) acetonitrile/H$_2$O); 3) a polyaromatic hydrocarbon mix with uracil (50 μg/mL), benzene (80 μg/mL), naphthalene (50 μg/mL), fenantreen (300 μg/mL), fluoranthene (50 μg/mL), 7,12 dimethylbenz[a]antraceen (300 μg/mL) diluted in 5050 (v/v) acetonitrile/H$_2$O; and 4) a general column test mixture containing uracil (20 μg/mL), caffeine (100 μg/mL), phenol (100 μg/mL), 1-phenyl-1-ethanone (100 μg/mL), propyl-4-hydroxybenzoate (100 μg/mL), benzene (500 μg/mL) and toluene (500 μg/mL) which was diluted in 4060 (v/v) acetonitrile/H$_2$O.

Two mobile phases are used: water (mobile phase A) and acetonitrile (mobile phase B). The following gradient profile is applied for the analysis of mixture 1): 0.5 minutes constant flow at 30% B, then from 30% to 100% B in 9.5 minutes; this composition is kept constant for 1.5 minutes before returning to the initial conditions in 0.5 min and column regeneration for 3 min, the flow rate is 0.15 mL/min. The following gradient profile is applied for the analysis of mixture 2): from 50% to 100% B in 5 minutes; this composition is kept constant for 2.5 minutes before returning to the initial conditions in 0.5 min and column regeneration for 6 min, the flow rate is about 0.20 mL/min. The following gradient profile is applied for the analysis of mixture mixture 3): from 50% to 100% B in 10 minutes; this composition is kept constant for 1 minute before returning to the initial conditions in 0.5 min and column regeneration for 5.5 min, the flowrate is about 0.2 mL/min. The sample volume is 0.5 µL. Detection is performed at 210 nm for the phenones and the polyaromatic hydrocarbons and at 254 nm for the paraben mixture. Test mixture 4) is used to compare the home packed column (5 cm×2.1 mm ID) and to compare the obtained results with three commercially available C-18 columns of the same length (5 cm), namely a Zorbax SB C-18 column from Agilent (ID 2.1 mm), a Luna C-18 (2) column from Phenomenex (ID 4.6 mm) and an X-Bridge C-18 column from Waters (ID 4.6 mm). Analyses are performed isocratically with 40% acetonitrile 60% water. The flow rate used is about 0.15 mL/min.

With the test mixtures as described above, a column comprising powders obtainable by the methods according to the present invention could show increased retention factors compared to commercial columns such as a Luna C-18(2) column, due to the larger carbon content of the material.

Polar Compounds

To test the retention capacity for polar compounds, a test mixture with polar pesticides can be made containing NaI (1 mg/mL), desethyl-2-hydroxyatrazine (200 µg/mL), desethyl desisopropyl atrazine (400 µg/mL), desisopropyl atrazine (50 µg/mL), aldicarb (50 µg/mL), cyanazine (50 µg/mL), simazine (400 µg/mL), prometryne (50 µg/mL), atrazine (50 µg/mL) and propazine (50 µg/mL) which is diluted in 5050 (v/v) acetonitrile/water. The analysis is performed isocratically at 0.1 mL/min with 20% acetonitrile 80% water with a sample volume of 0.5 µL and detection at 254 nm both on the home made column and a commercial Kinetex® column with 2.6 µm C18 particles (5 cm, 2.1 mm ID).

Columns comprising powders obtainable by the methods according to the present invention could show improved separation of these polar compounds compared to commercial products, such as the Kinetex® column described above.

Column Stability

To test the column stability a test cycle is set up with acid and base flushes. The following mobile phase were prepared: A1: 1 L of a 10 mM ammonium bicarbonate at pH 10.5 solution in water; B1: 2.5 L acetonitrile; A2: 2.5 L water; B2: 1 L of a 5050 water/acetonitrile with 0.5% of formic acid at pH 2 solution.

The following cycle of flushes and analyses can be performed on the column; the six steps may be repeated, for example 13 times.

Step 1: 24 times high pH flush procedure: (mobile phases A1 and B1)
The following gradient profile can be applied: from 5% to 95% B1 in 6 minutes; this composition is kept constant for 2 minutes before returning to the initial conditions in 1 min and column regeneration for 2 min, the flow rate is about 0.15 mL/min.

Step 2: high pH testing: (mobile phases A1 and B1)
The analysis can be performed isocratically with a 5050 composition of A1 and B1 at a flow rate of 0.15 mL/min with detection at 230 nm of a sample mixture of uracil (50 µg/mL) and diphenhylhydramine hydrochloride (300 µg/mL) diluted in 50% A1 and 50% B1 and a 0.5 µL injection volume. The injection is performed 3 times and the analysis may run for 10 minutes.

Step 3: 2 times neutral pH flush procedure: (mobile phases A2 and B1)
The following gradient profile can be applied: 2 minutes constant flow at 5% B1, then from 5% to 100% B1 in 3 minutes; this composition is kept constant for 5 minutes before returning to the initial conditions in 1 minute, the flow rate is about 0.15 mL/min. This step equilibrates the column for the next analysis prevents salt formation in step 4.

Step 4: neutral pH testing: (mobile phases A2 and B1)
The analysis can be performed isocratically with a 4060 composition of B1 and A2 at a flow rate of 0.15 mL/min with detection at 210 nm of a sample mixture 4) described above. The injection is done 3 times with an injection volume of 0.5 µL and an analysis time of 20 minutes.

Step 5: 24 times low pH flush procedure: (mobile phases A2 and B2)
The following gradient profile can be applied: from 5% to 95% B1 in 6 minutes; this composition is kept constant for 2 minutes before returning to the initial conditions in 1 minute and column regeneration for 2 min, the flow rate is about 0.15 mL/min.

Step 6: 2 times neutral pH flush procedure: (mobile phases A2 and B1)
The following gradient profile can be applied: 2 minutes constant flow at 5% B1, then from 5% to 100% B1 in 3 minutes; this composition is kept constant for 5 minutes before returning to the initial conditions in 1 minute, the flow rate is about 0.15 mL/min.

The stationary phase comprising the material according to the present invention could be stable against the harsh flushing conditions described above; thus, the stationary phase could withstand both high and low pH.

The invention claimed is:
1. A compound of formula (A):

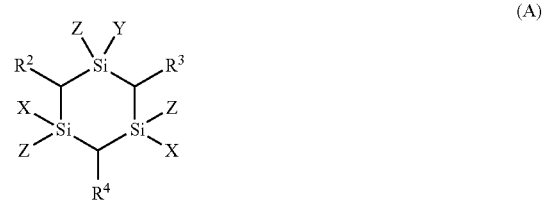

wherein X is $OR^1$, wherein $R^1$ is $C_{1-6}$alkyl;
Y is X or $-CHR^{13}Si(X)_{3-n}(Z)_n$, wherein n is 1 or 2;
Z is X or $C_{1-4}$alkyl; and
$R^2$, $R^3$, $R^4$ and $R^{13}$ are hydrogen or a hydrocarbon selected from the group consisting of $C_{3-30}$alkyl, $C_{6-10}$aryl, $C_{1-10}$alkyl$C_{6-10}$arylene, $C_{6-10}$aryl$C_{1-6}$alkylene, $C_{3-8}$cycloalkyl, $C_{2-30}$alkenyl, $C_{2-30}$alkynyl, and $C_{2-10}$alkenyl$C_{6-10}$arylene, said hydrocarbon being optionally substituted by one or more substituents;

with the proviso that $R^2$, $R^3$, $R^4$ and $R^{13}$ are not all hydrogen.

2. The compound according to claim 1, wherein said one or more substituents are independently selected from hydroxyl, epoxy, $C_{1-30}$thioalkyl, halo, amino, sulfhydryl, acyl, $C_{1-10}$alkoxy, $C_{1-6}$ alkyl, $C_{1-6}$ alkylamino, sulfophenyl, carboxyl, cyano, methylcyano, phenyl, 2,3-dihydroxypropyl, styryl, divinylphenyl, ethylvinylphenyl, pentafluorophenyl, sulfo, sulfonato, phosphonato, phosphinato, —SOCl, —NH$_3$R$^{12}$ wherein $R^{12}$ is a counterion, phenyloxy$C_{1-6}$alkyl, allylamino, allyl, benzoyloxy, tolyl, nitrophenyl, oxyphenyl, an ion exchange functionality, an embedded polar functionality and ethylpyridinyl.

3. A composition comprising a compound of formula (B) and a compound of formula (C):

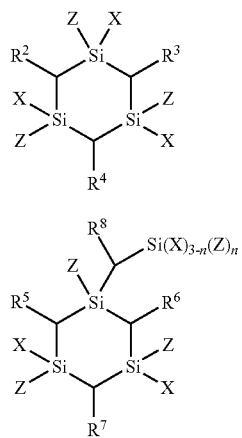

(B)

(C)

wherein X is $OR^1$, wherein $R^1$ is $C_{1-6}$alkyl;
n is 1 or 2;
Z is X or $C_{1-4}$alkyl; and
$R^2$, $R^3$, $R^4$, $R^5$, $R^6$, $R^7$ and $R^8$ are hydrogen or a hydrocarbon selected from the group consisting of $C_{3-30}$alkyl, $C_{6-10}$aryl, $C_{1-10}$alkyl$C_{6-10}$arylene, $C_{6-10}$aryl$C_{1-6}$ alkylene, $C_{3-8}$ cycloalkyl, $C_{2-30}$alkenyl, $C_{2-30}$alkynyl, and $C_{2-10}$alkenyl$C_{6-10}$arylene, said hydrocarbon being optionally substituted by one or more substituents;
with the proviso that $R^2$, $R^3$ and $R^4$ are not all hydrogen and $R^5$, $R^6$ $R^7$ and $R^8$ are not all hydrogen.

4. The composition according to claim 3, comprising compounds of formula (D), (E), (F), (G) and (H):

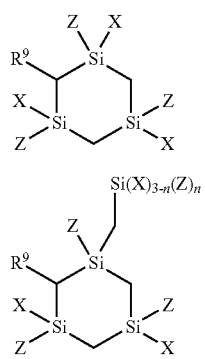

(D)

(E)

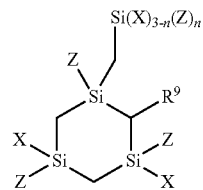

(F)

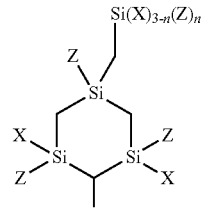

(G)

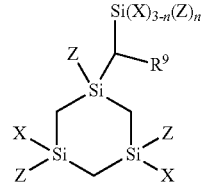

(H)

wherein X is $OR^1$, wherein $R^1$ is $C_{1-6}$alkyl;
n is 1 or 2;
Z is X or $C_{1-4}$alkyl; and
$R^9$ is a hydrocarbon selected from the group consisting of $C_{3-30}$alkyl, $C_{6-10}$aryl, $C_{1-10}$alkyl$C_{6-10}$arylene, $C_{6-10}$aryl$C_{1-6}$alkylene, $C_{3-8}$cycloalkyl, $C_{2-30}$alkenyl, $C_{2-30}$alkynyl, and $C_{2-10}$alkenyl$C_{6-10}$arylene, said hydrocarbon being optionally substituted by one or more substituents.

5. A material comprising [SiC]$_3$ ring compounds according to claim 1, wherein said [SiC]$_3$ rings are interconnected by oxygen atoms O via Si—O bonds.

6. The material according to claim 5, which is a porous material.

7. The material according to claim 5, formed as a powder, a film or a monolith.

8. The material according to claim 5, further comprising [SiC]$_3$ ring compounds of formula (I):

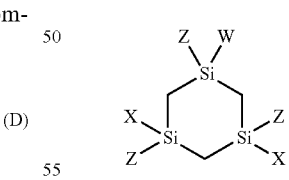

(I)

wherein X is $OR^1$, wherein $R^1$ is $C_{1-6}$alkyl;
W is X or —CH$_2$Si(X)$_{3-n}$(Z)$_n$, wherein n is 1 or 2;
Z is X or $C_{1-4}$alkyl;
wherein the [SiC]$_3$ rings of formula (A) and (I) are interconnected by oxygen atoms O via Si—O bonds.

9. The material according to claim 5, further comprising acyclic units SiO$_4$ or SiO$_3$R$^{10}$, wherein $R^{10}$ is $C_{1-6}$alkyl and wherein the [SiC]$_3$ rings and the acyclic units are interconnected by the O atoms.

10. A chromatography device having a stationary phase comprising the material according to claim 5.

11. A method for the preparation of a compound of formula (A):

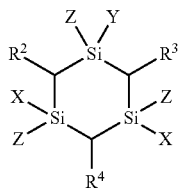

(A)

wherein X is $OR^1$, wherein $R^1$ is $C_{1-6}$alkyl;
Y is X or —$CHR^{13}Si(X)_{3-n}(Z)_n$, wherein n is 1 or 2;
Z is X or $C_{1-4}$alkyl; and
$R^2$, $R^3$, $R^4$ and $R^{13}$ are hydrogen or a hydrocarbon selected from the group consisting of $C_{3-30}$alkyl, $C_{6-10}$aryl, $C_{1-10}$alkyl$C_{6-10}$arylene, $C_{6-10}$aryl$C_{1-6}$alkylene, $C_{3-8}$cycloalkyl, $C_{2-30}$alkenyl, $C_{2-30}$alkynyl, and $C_{2-10}$alkenyl$C_{6-10}$arylene, said
hydrocarbon being optionally substituted by one or more substituents;
with the proviso that $R^2$, $R^3$, $R^4$ and $R^{13}$ are not all hydrogen;
said method comprising the reaction of a compound of formula (I):

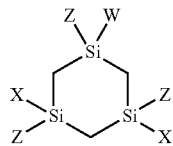

(I)

wherein W is X or —$CH_2Si(X)_{3-n}(Z)_n$, wherein n is 1 or 2;

with a compound Q-R, wherein Q is halo and R is a hydrocarbon selected from the group consisting of $C_{3-30}$alkyl, $C_{6-10}$aryl, $C_{1-10}$alkyl$C_{6-10}$arylene, $C_{6-10}$aryl$C_{1-6}$alkylene, $C_{3-8}$cycloalkyl, $C_{2-30}$alkenyl, $C_{2-30}$alkynyl, and $C_{2-10}$alkenyl$C_{6-10}$arylene, said hydrocarbon being optionally substituted by one or more substituents, in the presence of a strong base selected from IUPAC Group 1 metal alkyl compounds, IUPAC Group 1 metal aryl compounds, lithium diisopropylamide, lithium diethylamide, lithium dimethylamide, lithium dicyclohexylamide, sodium amide, lithium bis(trimethylsilyl)amide, sodium hydride, lithium hexamethyldisilazide and sodium hexamethyldisilazide.

12. A method for the preparation of a material comprising $[SiC]_3$ rings interconnected by oxygen atoms O via Si—O bonds, the method comprising polycondensing a compound according to claim 1 under conditions suitable for polycondensation of said compound, optionally in the presence of a template material selected from the group consisting of nonionic surfactants, ionic surfactants, colloidal crystals, polymers, hyper branched molecules, star-shaped molecules, macromolecules, dendrimers, and combinations thereof under conditions suitable for self-assembly of said compound and removing the template material from the self-assembled cyclic molecule.

13. The method according to claim 12, wherein said template material is selected from a poloxamer, a tetraalkylammonium salt, a nonionic polyoxyethylene alkyl and a Gemini surfactant.

14. The method according to claim 12, comprising spray-drying a composition comprising the compound and said template material.

* * * * *